United States Patent [19]

Hoegnelid

[11] Patent Number: 5,353,801
[45] Date of Patent: Oct. 11, 1994

[54] METHOD FOR PROCESSING AN ELECTRICAL SIGNAL, PARTICULARLY A SIGNAL DERIVED FROM A HEART

[75] Inventor: Kurt Hoegnelid, Västerhaninge, Sweden

[73] Assignee: Siemens Aktiengesellschaft, Munich, Fed. Rep. of Germany

[21] Appl. No.: 100,043

[22] Filed: Jul. 30, 1993

[30] Foreign Application Priority Data

Jul. 31, 1992 [EP] European Pat. Off. ........ 92113112.4

[51] Int. Cl.$^5$ .............................................. A61B 5/00
[52] U.S. Cl. ................... 128/696; 364/413.06; 364/413.05; 128/710
[58] Field of Search ................ 128/696, 710; 364/413.06, 413.05, 413.03, 413.02, 413.01

[56] References Cited

U.S. PATENT DOCUMENTS

| | | | |
|---|---|---|---|
| 4,567,883 | 2/1986 | Langer et al. | 128/696 |
| 5,014,284 | 5/1991 | Langer et al. | 128/696 |
| 5,058,599 | 10/1991 | Andersen | 128/705 |

FOREIGN PATENT DOCUMENTS 2123560  2/1984  United Kingdom .

OTHER PUBLICATIONS

"Reduction of ECG-Data Using a Microcomputer," Kraft et al. Biomedizinische Technik, vol. 25, No. 1/2 (Jan.-Feb. 1980), pp. 2-6.

"Biosignal Recognition Using Serial Data from a Delta Modulator," Heimer et al., IEEE Engineering in Medicine & Biology Society, 10th Annual Int. Conf., pp. 149-150.

"An Adaptive Real-Time ECG Compression Algorithm with Variable Threshold," Furth et al., IEEE Trans. on Biomed. Eng., vol. 35, No. 6, No. 6, Jun. 1988, pp. 489-494.

Primary Examiner—William E. Kamm
Assistant Examiner—Kennedy J. Schaetzle
Attorney, Agent, or Firm—Hill, Steadman & Simpson

[57] ABSTRACT

For compressing an electrical signal, such as a cardiac signal, converted by delta modulation into a binary operational sign signal, four data words are generated in the sequence of the appearance of four possible statuses, the four data words respectively defining the status and its duration. The statuses are defined in that the signal has a positive, minimum steepness during a minimum duration in a first status and has a negative minimum steepness in a second status. For a flatter signal curve, third and fourth statuses are respectively defined in which the signal rises or drops by a defined amount during the status duration.

7 Claims, 3 Drawing Sheets

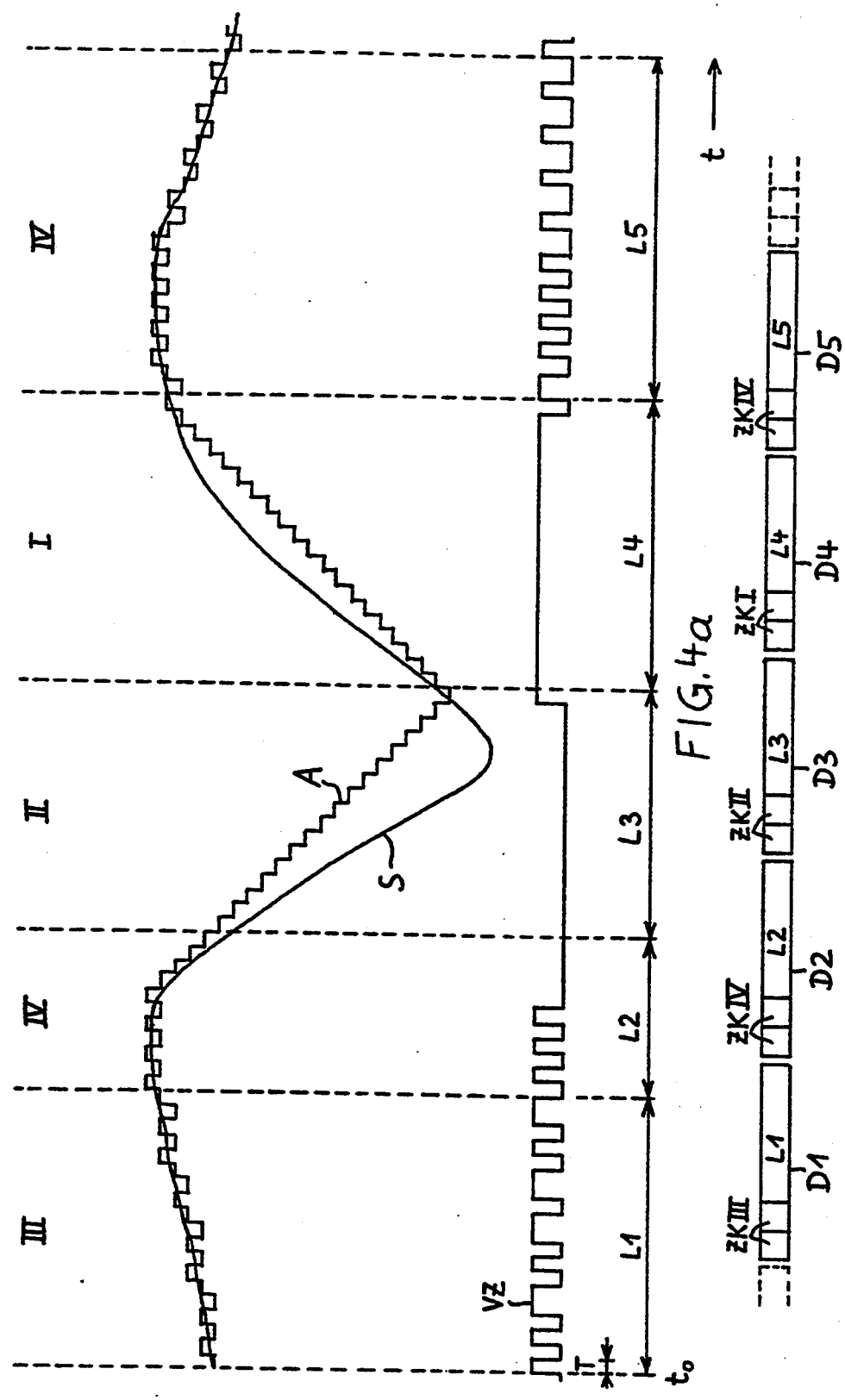

METHOD FOR PROCESSING AN ELECTRICAL SIGNAL, PARTICULARLY A SIGNAL DERIVED FROM A HEART

BACKGROUND OF THE INVENTION

1. Field of the Invention

The present invention is directed to a method for processing an electrical signal, particularly a signal derived from a heart, of the type wherein the electrical signal is converted by delta modulation into a binary signal composed of a pulse sequence having time-discrete, logic operational sign values of zero or one.

2. Description of the Prior Art

A method of this general type is disclosed, for example, by European Application 0 402 508 or U.S. Pat. No. 4,567,883, wherein an electrical signal derived from a heart is compared in a delta modulator to a signal referred to as a predictor signal, that has either a constant positive or a constant negative slope, and a binary operational sign signal having operational sign values of one and zero is generated at the output of the delta modulator dependent on whether the electrical signal upwardly or downwardly exceeds the predictor signal. A change of the predictor signal from the positive slope to the negative slope occurs given every operational sign change from one to zero, whereas the operation sign signal is modified in the opposite way given an operational sign change from zero to one. The binary operational sign signal at the output of the delta modulator thus indicates to what extent the electrical signal follows the predictor signal with the two different, constant slopes. In order to obtain a better matching of the predictor signal to the curve of the electrical signal, and thus to keep the modulation noise, i.e. the error differences between the electrical signal and the predictor signal, optimally low, it is additionally provided in the method disclosed by U.S. Pat. No. 4,567,883 that different amounts can be set for the slope of the predictor signal dependent on the operational sign signal at the output of the delta modulator.

It is often desirable for a further evaluation of the delta-modulated signal to first store the pulse sequence of the binary operational sign signal in a memory and to recall it as needed from the memory for the signal evaluation. An example of this is the storing of an intracardial electrogram digitized by delta modulation in a memory of an implantable heart pacemaker or defibrillator in order to be able to utilize the stored, intracardial electrogram for diagnostic or therapeutic purposes at a later time. To make a meaningful evaluation of the intracardial electrogram possible, the electrogram must usually be acquired over a longer time span and be stored, so that an extremely large data set to be stored arises. The memory capacity that can be realized in implantable devices, however, is limited due to the small structural size and the compact format of such devices.

SUMMARY OF THE INVENTION

It is therefore an object of the present invention to specify a method for compressing a delta-modulated electrical signal, particularly a signal derived from a heart.

The above object is achieved in accordance with the principles of the present invention in a method of the type initially cited, wherein the pulse sequence is converted into four different data words that are respectively generated in immediate succession in the sequence of the occurrence of four possible statuses. A first data word indicates a first status identifier and the length (duration) of a first status wherein the operational sign signal continuously has the logical value of zero for a prescribed, first minimum duration. A second data word indicates a second status identifier and the length of a second status wherein the operational sign signal continuously has the logical value of one for a prescribed, second minimum duration. A third data word indicates a third status identifier and the length of a third status wherein the operational sign value changes within the prescribed minimum duration and the sum of all operational sign values of one exceeds the sum of all operational sign values of zero by a prescribed, first amount. A fourth data word indicates a fourth status identification and the length of a fourth status wherein the operational sign value changes within the prescribed minimum durations and the sum of all operational sign values of zero exceeds the sum of all operational sign values of one by a prescribed, second amount.

With the assistance of the four data words, the curve of the electrical signal is thus described as a sequence of four different statuses, each of which can be of a different length. The first status is characterized by the electrical signal exceeding the positively rising predictor signal of the delta modulator over a longer chronological duration, i.e., the signal has a specific, positive minimum steepness, whereas the electrical signal in the second status falls below the negatively descending predictor signal, likewise over a longer chronological duration, i.e. has a defined, negative minimum steepness. Given a flatter curve of the electrical signal, the third status indicates that the electrical signal has risen on average by the first, prescribed amount over the duration of this status, whereas the electrical signal in the fourth status has decreased on average by the prescribed, second amount.

In order to simplify the method of the invention, and thus to reduce the computationally or hardware outlay required for the implementation of the method, identical values are preferably provided for the first and second minimum durations.

Correspondingly, identical values can also be provided for the first and second amounts.

The lengths of the respective statuses are defined in the simplest way by counting the number of time-discrete operational sign values appearing during these statuses in a counter.

Due to counting functions being simply realizable in terms of both program and hardware, in a further embodiment of the invention that the appearance of the operational sign values is counted in a further counter in order to identify whether the sum of the operational sign values of one upwardly or downwardly exceeds the sum of the operational sign values of zero by the prescribed amounts. The operational sign values are counted in the further counter with a counting direction that can be switched dependent on the respective operational sign values of zero or one until the count value upwardly or downwardly exceeds one of the prescribed amounts.

As already described in conjunction with U.S. Pat. No. 4,567,883, the modulation noise in delta modulation, wherein the operational sign signal is generated dependent upon whether the electrical signal upwardly or downwardly exceeds a predictor signal variable in different directions with a prescribed variation amount, the different variation amounts for the predictor signal can be adjustable dependent on the operational sign signal. The data words then each additionally contain an information packet (bit sequence) that identifies the currently set variation amount.

DESCRIPTION OF THE DRAWINGS

FIG. 4a is a diagram showing another example of the electrical signal for explaining the invention.

FIG. 4b shows and the conversion of the signal of FIG. 4a into data words in accordance with the invention.

DESCRIPTION OF THE PREFERRED EMBODIMENTS

Figure 1:
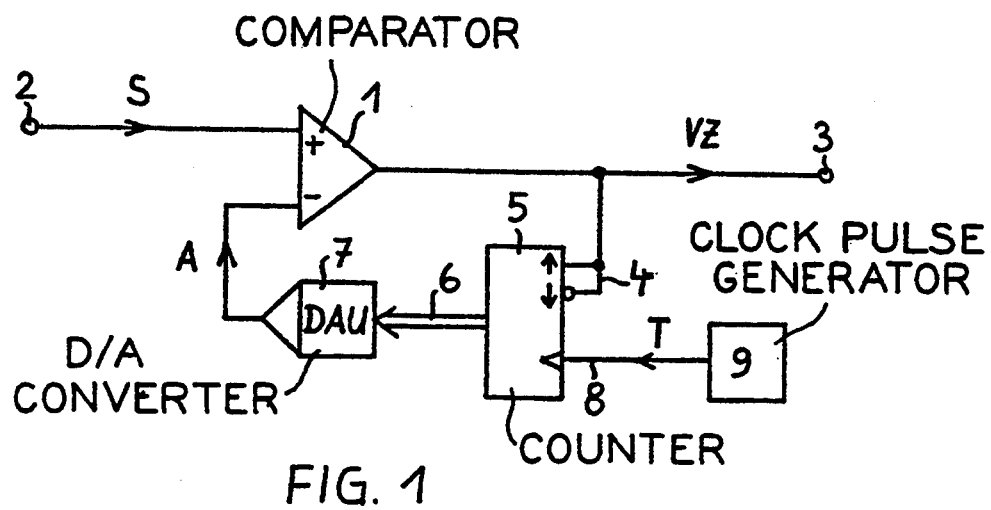
FIG. 1 is an exemplary embodiment of a delta modulator for use in practicing the present invention.

FIG. 1 shows a simple exemplary embodiment of a delta modulator having a comparator 1 that is connected via a first, non-inverting input (+) to an input 2 of the delta modulator. An electrical signal S, for example an electrocardiogram, to be converted into a binary operational sign signal VZ is supplied to the input Z. The output 3 of the comparator 1 is connected to a control input 4 of a counter 5, whose output 6 is connected via a digital-to-analog converter 7 to a second, inverting input (−) of the comparator 1. The counter 5 is connected to a clock signal generator 9 via a clock input 8.

The output 3 of the comparator 1 always assumes the logic status of one when the electrical signal S at the non-inverting input (+) exceeds the output value A of the digital-to-analog converter 7. (The output A constitutes the aforementioned predictor signal, in analog form.) When, by contrast, the electrical signal S falls below the output value A of the digital-to-analog converter 7, then the output 3 of the comparator 1 assumes the logic status of zero. The counter 5 continuously counts the pulses clock of the clock signal T generated by the clock signal generator 9. The counting direction is controlled via the control input 4 dependent on the prevailing logic status at the output 3 of the comparator 1 such that the counter 5 increments when the logic status has the value of one and decrements when the logic status is zero. In this way, the counter 5 generates a digital count signal at its output 6 that, after being converted in the analog predictor signal A, is compared in the comparator 1 to the electrical signal S and, dependent on the deviation of the electrical signal S compared thereto, is either upwardly or downwardly adapted to the electrical signal S. The count signal, or the predictor signal A that is analogous thereto, thereby follows the electrical signal S with a step-shaped curve, whereby the step height is established by the counting increment and the step width is established by the clock of the clock signal T. The operational sign signal VZ at the output 3 of the comparator 1 indicates the current counting direction, and thus the direction of the adaptation of the analog predictor signal A to the electrical signal S.

Figure 2:
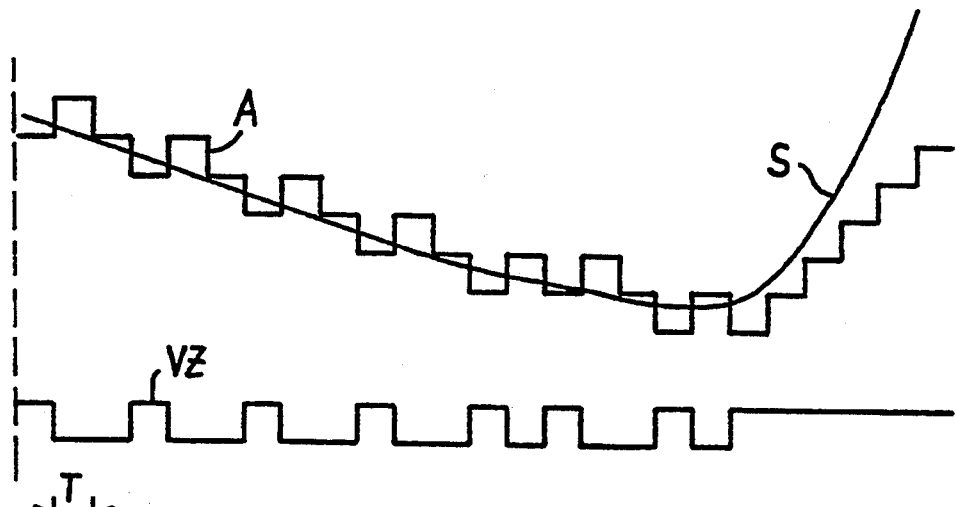
FIG. 2 is a diagram showing an example of the electrical signals supplied to the delta modulator and showing the binary operational sign signal the delta modulator generates at its output side.

FIG. 2 shows examples of the curve of the electrical signal S, the resulting analog predictor signal A generated by the digital-to-analog converter 7, and the resulting operational sign signal VZ at the output 3 of the comparator 1.

Figure 3:
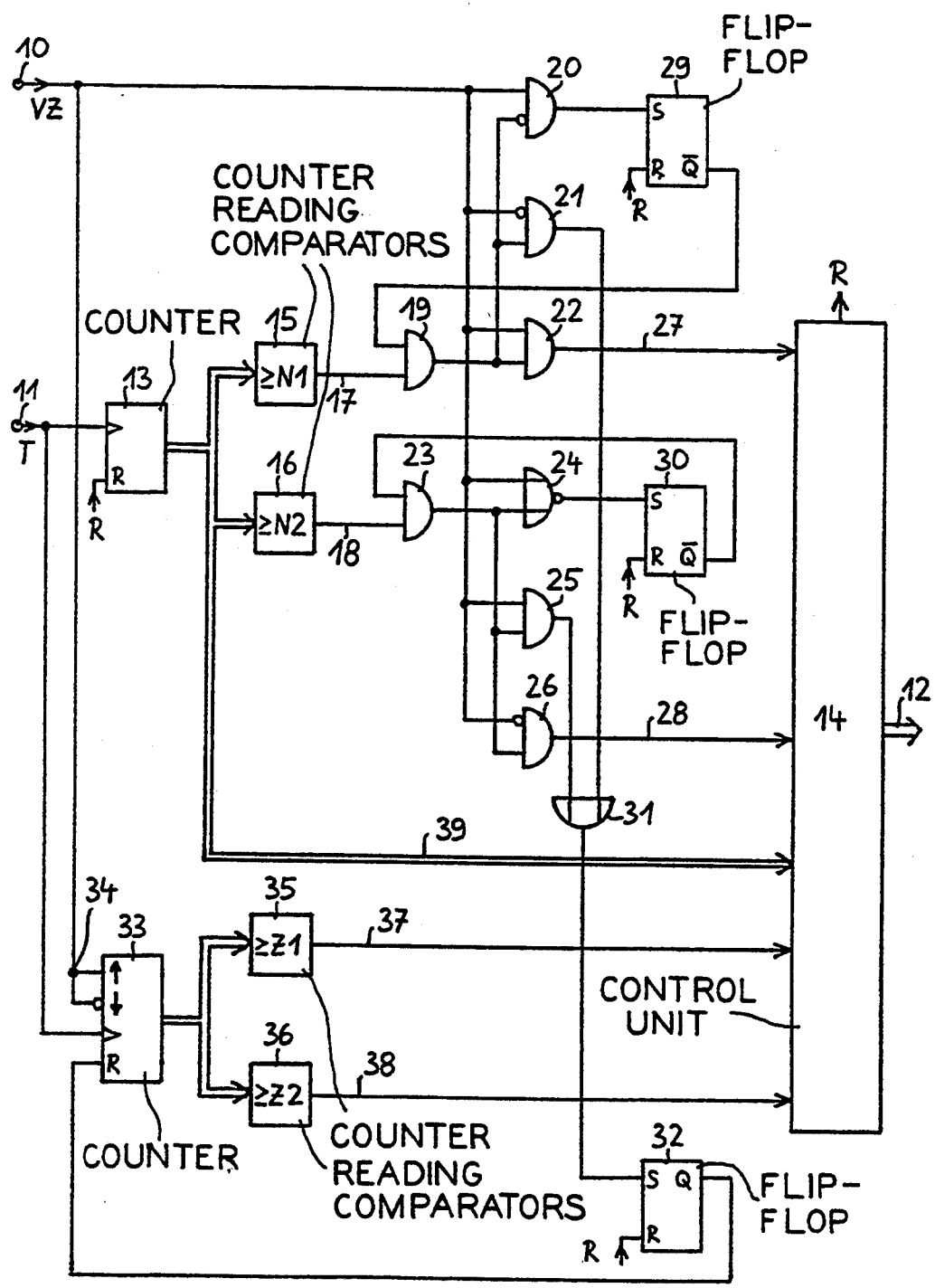
FIG. 3 is an exemplary embodiment of a circuit arrangement for realizing the method of the invention.

FIG. 3 shows a circuit arrangement for the realization of the method of the invention. The circuit arrangement has a first input 10 for the operational sign signal VZ obtained from the output 3 of the delta modulator of FIG. 1, a second input 11 for the clock signal T from the clock signal generator 9 and which prescribes the time grid for the logic operational sign values of zero and one of the operational sign signal VZ, and an output 12 at which the operational sign signal VZ compressed into data words is present as an output signal.

The clock signal T is supplied to a counter 13 which can be reset via a control output R of a control unit 14 to an initial counter reading of zero, and which increments its counter reading corresponding to the clock of the clock signal T. The counter reading of the counter 13 is supplied to a first counter reading comparator 15 and to a second counter reading comparator 16. The counter reading comparator 15 generates an output signal, i.e., a logic one, at its output 17 when the counter reading upwardly exceeds a prescribed comparison value N1. The second counter reading comparator 16 generates an output signal at its output 18 when the counter reading upwardly exceeds another prescribed comparison value N2. The output 17 of the first counter reading comparator 15 is connected via an AND-element 19 to one input of each of three logical elements 20, 21 and 22 whose second inputs are charged with the operational sign signal VZ. The output 18 of the second counter reading comparator 16 is connected via a further AND-element 23 to one input of each of three further logic elements 24, 25 and 26, whose second inputs are likewise charged with the operational sign signal VZ.

The logic elements 20–22 and 24–26 respectively generate an output signal under the following conditions. The logic element 20 generates an output signal when the operational sign signal VZ assumes the value of one before the counter reading of the counter 13 has reached the first comparison value N1. The logic element 21 generates an output signal when the operational sign signal VZ has the value of zero and the counter reading of the counter 13 has reached or upwardly exceeded the comparison value N1. The logic element 22 generates an output signal when the counter reading of the counter 13 has reached or upwardly exceeded the first comparison value N1 and the operational sign signal VZ assumes the value of one. The logic element 24 generates an output signal when the operational sign signal VZ assumes the value of zero before the counter reading of the counter 13 has reached the second comparison value N2. The logic element 24 generates an output signal when the operational sign signal VZ has the value of one and the counter reading of the counter 13 has reached or upwardly exceeded the second comparison value N2. Finally, the logic element 26 generates an output signal when the counter reading of the counter 13 has reached or upwardly exceeded the second comparison value N2 and the operational sign signal VZ assumes the value of zero.

The outputs of the logic elements 22 and 26 are each connected to the control unit 14 via respective control lines 27 and 28. The output of the logic element 20 is connected to the setting input S of a first flip-flop 29 that has its inverting output $\overline{Q}$ connected to a further input of the AND-element 19 following the first counter reading comparator 15. The output of the logic element 24 is correspondingly connected to the setting input S of a second flip-flop 30 that has its inverting output $\overline{Q}$ connected to a further input of the AND-element 23 following the second counter reading comparator 16. The outputs of the logic elements 21 and 25 are connected via an OR-element 31 to the setting input S of a third flip-flop 32, whose non-inverting output Q is connected to the reset input R of a further counter 33. The flip-flops 29, 30 and 32 can be reset via the control output R of the control unit 14.

The further counter 33 has a counter input charged with the clock signal T and a control input 34 charged with the operational sign signal VZ by means of which the counting direction can be switched so that the counter 33 increments given an operational sign value of one and decrements given an operational sign signal of zero. The counter reading of the further counter 33 is supplied to a third counter reading comparator 35 and to a fourth counter reading comparator 36. The third counter reading comparator 35 generates an output signal at its output 37 when its counter reading upwardly exceeds a third, prescribed comparison value Z1. The fourth counter reading comparator 36 generates an output signal at its output 38 when its counter reading downwardly exceeds a prescribed, fourth, negative comparison value $-Z2$. The outputs 37 and 38 of the counter reading comparators 35 and 36 are each respectively connected to the control unit 14. Finally, the output of the first counter 13 is likewise connected to the control unit 14 via a control line 39.

FIGS. 4a and 4b shall be referenced below for explaining the functioning of the circuit arrangement of FIG. 3. FIG. 4a shows a ORS complex from an electrocardiogram as an example of the electrical signal S. Further, the predictor signal A is shown at the output of the digital-to-analog converter 7 (FIG. 1) and the operational sign signal VZ is also shown.

At a starting time $t_0$, the counters 13 and 33 and the flip-flops 29, 30 and 32 are reset. It is assumed for the described example that the comparison values N1, N2, Z1 and $-Z2$ all have the same amount "4". At the first clock of the clock signal T, the electrical signal S exceeds the predictor signal A, so that the operational sign signal VZ has the logical value of one. It is therefore assumed that the electrical signal S rises thereafter. Since the counter 13 incremented by the clock signal T has not yet reached the count value N1=4, the flip-flop 29 is set by the logic element 20, assumes the value one at its inverting output $\overline{Q}$ and the AND-element 19 is thereby caused to inhibit the output 17 of the first counter reading comparator 15.

As a result of the operational sign value of one of the operational sign signal VZ, the predictor signal A is raised by one step at the next clock pulse, whereby the predictor signal A exceeds the electrical signal S and effects a change of the operational sign signal VZ to the operational sign value of zero. Since the counter 13 has not yet reached the count value N2=4, the flip-flop 30 is set via the logic element 24, which inhibits the output 18 of the second counter reading comparator 16 via its inverting output $\overline{Q}$ and the AND-element 23. The inhibiting of the outputs 17 and 18 of the two counter reading comparators 15 and 16 takes into consideration the fact that the operational sign signal has changed its operational sign value before the count values N1=N2=4 have been reached, and therefore precludes the electrical signal S from having a steeper curve over a longer time span than the maximally possible positive or negative slope of the predictor signal A due to the step height.

Beginning with the first clock, the counter reading of the further counter 33 is incremented at every operational signal value of one and is decremented at every operational sign value of zero. After a total of 19 clocks, the counter reading of the further counter 33 thereby reaches the comparison value Z1=4, so that the third counter reading comparator 35 supplies a control signal to the control unit 14 via its output 37. This control unit 14 polls the counter reading of the counter 13 in response thereto, which has the value "19" and thus indicates the length L1 of a status III during which the electrical signal S has risen with a slope that is lower on average than the maximally possible steepness of the predictor signal A, the signal S having risen overall by the amount Z1=4. For indicating this status III, the control unit 14 generates a data word D1 (FIG. 4b) at its output 12, whose two first bit places indicate a status identification ZKIII for the status III and whose other bit places indicate the length L1 of the status III.

Simultaneously with the generation of the data word D1, the counters 13 and 33 and the flip-flops 29, 30 and 32 are reset by the control unit 14. Also, the subsequent clock pulses of the clock signal T cause the operational sign value of the operational sign signal VZ to change before the counter reading of the counter 13 has reached one of the two comparison values N1 or N2. After a total of eleven clock pulses this time, the counter reading of the further counter 13 reaches the comparison value $-Z2$ of the fourth counter reading comparator 36, so that the comparator 36 supplies an output signal to the control unit 14 at its output 38. In response thereto, the control unit 14 again polls the counter reading of the counter 13. This has the value "11" and thus indicates the length L2 of a status IV during which the electrical signal S has dropped by the amount Z2=4 with a slope that is less on average than the maximally possible, negative steepness of the predictor signal A. In response thereto, the control unit 14 generates a new data work D2 (FIG. 4b) whose first two bit places contain a status identifier ZKIV for the status IV and whose other bit places indicate the length L2 of the status IV.

Simultaneously with the generation of the data word D2, the counters 13 and 33 and the flip-flops 29, 30 and 32 are reset by the control unit 14. At the first clock pulse of the clock signal T following the resetting, the electrical signal S downwardly exceeds the predictor signal A, so that the operational sign signal VZ has the logical value of zero. As a consequence, the output 18 of the second counter reading comparator 16 is inhibited via the logic element 24, the flip-flop 30 and the AND-element 23. The operational sign value of the operational sign signal VZ also does not change during the following clock pulses, so that the counter reading of the first counter 13 reaches the comparison value N1 of the first counter reading comparator 15 after four clock pulses. In response, the counter reading comparator 15 generates an output signal at its output 17 which sets the further flip-flop 32 via the logic element 21 and the OR-element 31. This further flip-flop 32 resets the second counter 33 via its non-inverting output Q. The clock pulses of the clock signal T continue to be counted in the first counter 13 until the operational sign signal VZ changes its operational sign value from zero to one. This change is detected by the logic element 22 and is reported to the control unit 14 via the control line 27. In response, the control unit 14 polls the counter reading of the counter 13, which has the value "17" in the illustrated exemplary embodiment, and thus indicates the length L3 of a status II during which the electrical signal S decreases with a slope that is greater on average than the steepness of the steps of the predictor signal A. The controllable switch unit 14 thereupon generates a data word D3 (FIG. 4b) at its output 12 whose first two bit places contain a status identifier ZKII for the status II and whose remaining bit places indicate the length L3 of the status II.

Simultaneously with the generation of the data word D3, the counters 13 and 33 and the flips flops 29, 30 and 32 are reset by the control unit 14. During the following clock pulses of the clock signal T, the electrical signal S exceeds the predictor signal A, until a change of the operational sign signal VZ from the operational sign value one to the operational sign value zero ensues at the twentieth clock pulse. This operational sign change is detected by the logic element 26 and is communicated to the control unit 14 via the control line 28. In response, the control unit 14 polls the counter reading of the counter 13, which has the value "20", and thus indicates the length L4 of a status I during which the electrical signal S has a greater slope on average than the steepness of the steps of the predictor signal A. The control unit 14 generates a data word D4 (FIG. 4b) at its output, whose two first bit places contain a status identifier ZKI for the status I and whose remaining bit places indicate the length L4 of the status I.

Following the status I, a status IV again occurs, whereby the electrical signal S has a comparatively flat curve and drops by the amount −Z2 over the duration L5 of this status IV. This new status IV is identified by a data word D5 (FIG. 4b) whose first two bit places again contain a status identifier ZKIV for the status IV and whose remaining bit places indicate the length L5 of this status IV.

As a result of the recited method, thus, the operational sign signal VZ at the output of the delta modulator is compressed into data words D1–D5 which respectively indicate one of the four possible statuses I–IV and its length L1–L4. During the statuses I and II, the average slope of the electrical signal S is greater than the maximally possible positive or negative slope of the predictor signal A, whereas the electrical signal S has less of an average steepness in the statuses III and IV and thereby rises overall by the amount Z1, or drops overall by the amount Z2.

The circuit arrangement in FIG. 3 is to be merely considered as an example for the implementation of the method of the invention, which can also be realized by the execution of a program.

Although modifications and changes may be suggested by those skilled in the art, it is the intention of the inventor to embody within the patent warranted hereon all changes and modifications as reasonably and properly come within the scope of his contribution to the art.

I claim as my Invention:

1. A method for processing an electrical signal comprising the steps of:
    converting said electrical signal by delta modulation into a binary operational sign signal composed of a pulse sequence having time-discrete logic operational sign values of zero or one;
    converting said pulse sequence into four different data words respectively generated in immediate succession in a sequence of appearance of four possible statuses of said pulse sequence;
    generating said first data word to indicate said first status and the length of said first status wherein the operational sign of said pulse sequence continuously has a logic value of zero for a selected, first minimum duration;
    generating said second data word to indicate said second status and the length of said second status wherein the operational sign value of said pulse sequence continuously has the logic value of one for a selected, second minimum duration;
    generating said third data word to indicate a third status and the length of said third status wherein the operational sign of said pulse sequence changes within a selected one of said first or second minimum durations and the sum of all operational sign values of one upwardly exceeds the sum of all operational sign values of zero by a selected, first amount; and
    generating said fourth data word to indicate said fourth status and the length of said fourth status wherein the operational sign value of said pulse sequence changes within a selected one of said first or second minimum durations and the sum of all operational sign values of zero upwardly exceeds the sum of all operational sign values of one by a selected, second amount.

2. A method as claimed in claim 1 comprising the additional step of deriving said electrical signal from a heart.

3. A method as claimed in claim 1 comprising the additional step of selecting identical values for said first and second minimum durations.

4. A method as claimed in claim 1 comprising the additional step of selecting identical values for said first and second amounts.

5. A method as claimed in claim 1 comprising the step of counting the number of time-discrete operational sign values of said pulse sequence in a counter for identifying the respective lengths of said first, second, third and fourth statuses.

6. A method as claimed in claim 5 comprising the additional steps of:
    counting said operational sign values of said pulse sequence in a further counter having a switchable counting direction;
    switching said counting direction of said further counter dependent on whether said operational sign value is zero or one for identifying whether the sum of all of said operational sign values of one upwardly or downwardly exceeds said sum of all operational sign values of zero respectively by said first and second amounts; and
    counting in said further counter until a count value of said further counter upwardly exceeds said first amount or downwardly exceeds said second amount.

7. A method as claimed in claim 1 wherein the step of converting said electrical signal by delta modulation into said binary operational sign signal is further defined by the steps of:
    generating a binary predictor signal which follows said electrical signal by changing from one binary state to another binary state when said electrical signal changes by a selected change amount within a specified period of time;

selecting said change amount generating said operational sign signal dependent on whether said electrical signal upwardly or downwardly transgresses a variable of said predictor signal with said selected change amount in different sign directions; and including an information sequence in each of said first, second, third and fourth data words identifying the currently selected change amount.

* * * * *